US006771374B1

United States Patent
Rangarajan et al.

(10) Patent No.: US 6,771,374 B1
(45) Date of Patent: Aug. 3, 2004

(54) SCATTEROMETRY BASED MEASUREMENTS OF A ROTATING SUBSTRATE

(75) Inventors: Bharath Rangarajan, Santa Clara, CA (US); Bhanwar Singh, Morgan Hill, CA (US); Michael K. Templeton, Atherton, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 221 days.

(21) Appl. No.: 10/050,758

(22) Filed: Jan. 16, 2002

(51) Int. Cl.$^7$ ............................................. G01N 21/55
(52) U.S. Cl. .................... 356/445; 356/237.1; 356/369; 427/165; 427/166; 428/64.1; 428/64.2
(58) Field of Search ................................ 356/445, 369, 356/237.1, 237; 427/165, 166; 428/64.1, 64.2, 64

(56) References Cited

U.S. PATENT DOCUMENTS 4,592,939 A * 6/1986 Temple et al. ................ 428/64
6,151,116 A * 11/2000 Hirosawa ..................... 356/369

* cited by examiner

Primary Examiner—Audrey Chang
Assistant Examiner—Craig Curtis
(74) Attorney, Agent, or Firm—Amin & Turocy, LLP

(57) ABSTRACT

A system and method are disclosed for monitoring characteristics of a rotating substrate. As the substrate rotates in an environment, an incident light beam is emitted onto the substrate near an axis about which the substrate rotates. The emission of the incident beam is controlled as a function of the angular orientation of the substrate, so that the incident beam selectively interrogates a central region of the substrate to facilitate measuring and/or inspecting characteristics of the substrate.

22 Claims, 8 Drawing Sheets

SCATTEROMETRY BASED MEASUREMENTS OF A ROTATING SUBSTRATE

TECHNICAL FIELD

The present invention relates to semiconductor processing and, more particularly, to a system and method for monitoring characteristics of a rotating substrate.

BACKGROUND

In the semiconductor industry, there is a continuing trend toward higher device densities. To achieve these higher densities, efforts continue toward scaling down device dimensions (e.g., at sub-micron levels) on semiconductor wafers. To accomplish such high device packing densities, smaller and smaller feature sizes are required. This may include the width and spacing of interconnecting lines, spacing and diameter of contact holes, and the surface geometry such as corners and edges of various features.

The process of manufacturing semiconductors, or integrated circuits, typically consists of more than a hundred steps, during which numerous of copies of an integrated circuit may be formed on a single wafer. Generally, the process involves creating several patterned layers on and into the substrate that ultimately form the complete integrated circuit. Fabricating a semiconductor using such sophisticated manufacturing techniques may involve a series of steps including cleaning, thermal oxidation or deposition, masking, etching, and doping.

Wafers may be pre-cleaned using, for example, high-purity, low-particle chemicals. Silicon wafers may be heated and exposed to ultra-pure oxygen in diffusion furnaces under carefully controlled conditions to form a silicon dioxide film of uniform thickness on the surface of the wafer.

A masking step is utilized to protect one area of the wafer while working on another area. This process typically includes photolithography or photo-masking. A photoresist or light-sensitive film is applied to the wafer, such as while supported in a suitable spin coating apparatus. A photoaligner aligns the wafer to a mask and then projects an intense light through the mask and through a series of reducing lenses, exposing the photoresist with the mask pattern.

The wafer is then "developed" (the exposed photoresist is removed), such as by applying a developing solution while rotating the substrate on a suitable support. The developed substrate may then be thermally baked to harden the remaining photoresist pattern. It is then exposed to a chemical solution or plasma (gas discharge) so that areas not covered by the hardened photoresist may be etched away. The photoresist is removed using additional chemicals or plasma. In order to ensure correct image transfer from the mask to the top layer, various wafer inspection methodologies may be employed.

Various process conditions affect formation of layers during semiconductor fabrication. Such conditions further can vary from batch to batch, which variations tend to cause inconsistencies in the resulting products. For example, a non-uniform film thickness can introduce overlay errors and other defects that can adversely affect a resulting integrated circuit formed on the substrate. Accordingly, measurement and inspection systems and techniques have been developed to analyze characteristics of a substrate in between different processing stages. However, when fatal defects are detected after a particular process has completed, structures having such defects typically have to be discarded.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides a system and method for monitoring characteristics of a substrate. The substrate is supported on a moveable support, such as adapted to rotate about an axis during part of a fabrication process. A measuring system is operable to emit an incident beam onto gratings and/or features of the substrate near the axis about which the substrate is rotating. The beam interacts with the substrate to produce a reflected and/or diffracted beam(s). The reflected and/or diffracted beam can be analyzed to determine substrate characteristics. In order to facilitate measuring feature characteristics, in accordance with an aspect of the present invention, the measuring system emits the incident beam as a function of the rotation of the moveable support such as to interrogate the gratings and/or features at a desired angle relative to the incident beam. As a result, the incident beam is able to selectively interrogate gratings and/or features on the substrate, thereby mitigating errors due to movement of the substrate.

Another aspect of the present invention provides a system for measuring characteristics of a substrate. The system includes a positioning system having a support for receiving a substrate and rotating about a rotational axis. A measurement system includes a light source. When the light source is activated, the light source emits light onto a central region of the substrate based on the angular orientation of the rotating substrate.

Another aspect of the present invention provides a method for measuring characteristics of a substrate. The substrate is rotated about an axis that extends through the substrate while supported within a processing environment. An incident light beam is emitted onto the substrate near the axis. The incident light beam is emitted based on the angular orientation of the substrate. As a result, the incident beam can selectively interrogate the substrate near the axis when the substrate is at a desired angular orientation relative to the incident beam.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION

The present invention provides a system and method for monitoring characteristics of a rotating substrate. The substrate is supported on a moveable support, such as adapted to rotate the substrate about an axis extending through the substrate and associated support. A measuring system is operable to emit an incident beam to a portion of the substrate near the axis to interrogate the surface of the substrate. Such interrogation produces a reflected and/or diffracted beam(s) that has beam properties indicative of substrate characteristics. In order to facilitate measuring feature characteristics, in accordance with an aspect of the present invention, the measuring system selectively emits the incident beam as a function of the position and/or rotation of the moveable support so as to facilitate interrogation of the central portion when at a desired angular orientation relative to the incident beam. As a result, the beam is able to selectively interrogate gratings and/or features on the substrate during such interrogation, thereby mitigating errors due to rotation of the substrate.

Figure 1:
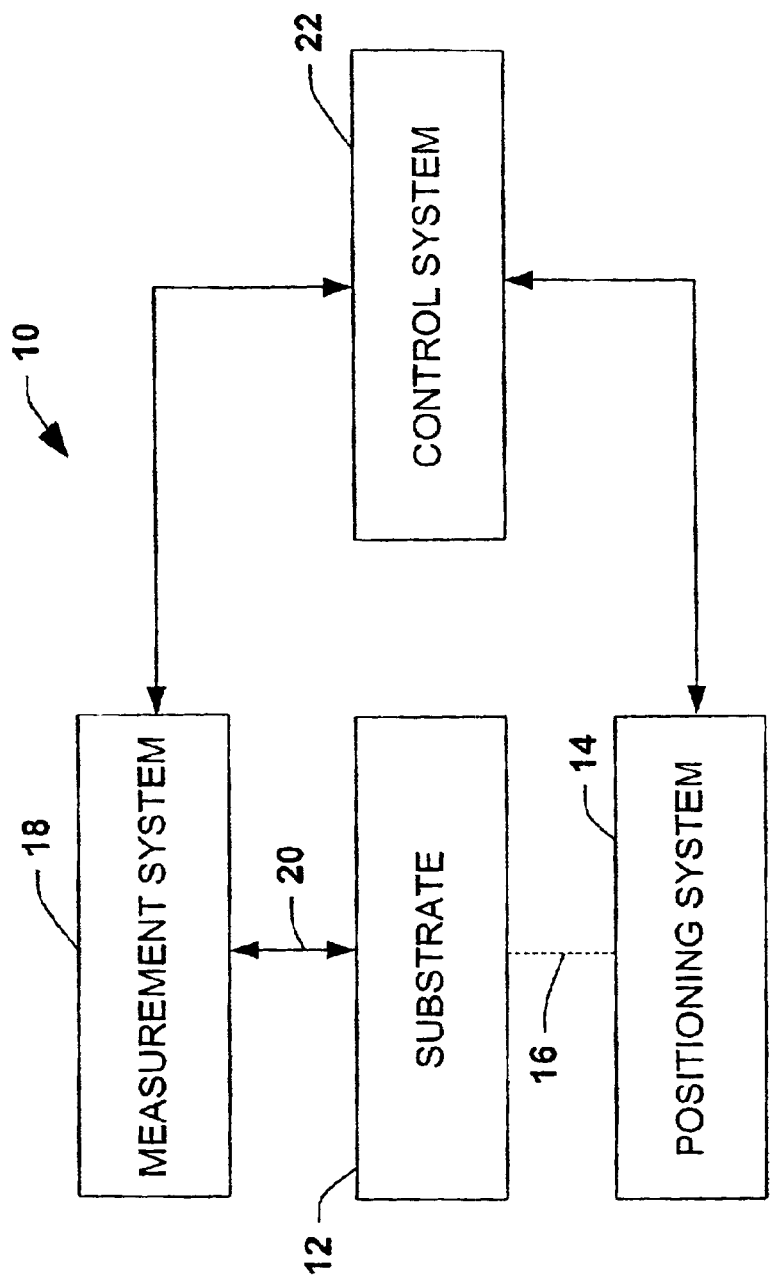
FIG. 1 is a simplified block diagram of a monitoring system in accordance with the present invention.

Turning now to FIG. 1, a block diagram of a measuring system 10 is illustrated for measuring characteristics of a substrate 12 in accordance with an aspect of the present invention. The substrate 12 is operatively connected to a positioning system 14 through a moveable support (e.g., a chuck), schematically indicated at 16. By way of example, the positioning system 14 is operable to rotate the support 16 about a central axis thereof. The central axis of the support extends through a known region of the substrate 12. Thus, as the support rotates about its axis, the substrate also rotates about the known region thereof (hereinafter generally referred to as "the central region" of the substrate). The rotation of the substrate 12 may be in connection with one or more processing steps, such as, for example, part of a deposition, etching or developing process.

The system 10 also includes a measurement system 18 operable to measure characteristics of the substrate 12 in accordance with an aspect of the present invention. The measurement system 18, for example, includes a light source that emits an incident beam 20 onto the central region of the substrate 12. When the beam 20 is emitted, it interacts with the substrate 12 and is diffracted and/or reflected.

The measurement system 18 also includes a detection system, such as a spectrometer, for detecting the reflected and/or diffracted beam (also indicated at 20 for sake of brevity) from the substrate 12. The reflected beam 20 can be reflected from or pass through relative to the substrate 12. Characteristics of the substrate 12 are determined based on the properties of the reflected and/or diffracted beam 20. Those skilled in the art will understand and appreciate various other non-destructive optical measurement techniques that could be utilized.

The system 10 includes a control system 22 operatively coupled to the positioning system 14 and to the measurement system 18. The control system 22 is programed and/or configured to control operation of the positioning system 14 and the measurement system 18 in accordance with an aspect of the present invention.

According to one particular aspect, the control system 22 can control the measurement system 18 to intermittently emit the incident beam 20 as a function of the angular position of the substrate 12, such that the incident beam is emitted in synchronization with the rotation of the substrate about its axis. The control system 22 can receive rotation information indicative of substrate rotation (e.g., position and/or velocity information) from the positioning system 14. Alternatively, registration means (e.g., alignment markers, apertures, reflectors, etc.) could be provided at the substrate to facilitate a determination of the angular orientation of the substrate 12 relative to the measurement system 18.

The control system 22 can employ the rotation information to control operation of the measurement system 18 so that the incident beam 20 selectively interrogates a given grating or different gratings and/or substrate features at a central location of the substrate 12 near the rotational axis. For example, the incident beam 20 can be emitted to selectively interrogate the substrate 12 when central gratings have a desired angular orientation relative to the incident beam, such that the beam can capture the gratings at a desired angle. In a particular aspect, the control system 22 controls the measurement system 18 to pulse the incident beam 20 to an ON condition when the central gratings are oriented generally normal relative to the incident beam and turn the beam to an OFF condition when the desired orientation does not exist. Additionally or alternatively, the detector of the measurement system can be controlled to detect the reflected beam 20 as a function of the position or movement of the substrate, which is determined from position/velocity data provided by the positioning system 14. The central gratings can be located between imaging patterns or be placed at a desired central location in place of a pattern on the substrate.

Alternatively or additionally, the control system 22 can control the positioning system 14 to rotate the support 16 and the substrate 12 as a function of the beam emission from the measurement system 18, such that the substrate is rotated in synchronization with the beam emission. For example, the incident beam 20 may be intermittently emitted (e.g., pulsed using a strobe technique) onto the substrate 12 at a known rate. The control system 22 may, in turn, employ a feedback/feedforward control signal to the positioning system 14 for controlling rotation of the substrate 12 so that the beam 20 selectively interrogates a given grating or different gratings at the central region of the substrate where the gratings.

By controlling the relative orientation between the incident beam 20 and the grating pattern, in accordance with an aspect of the present invention, interaction between the beam and the substrate 12 is facilitated so that the reflected and/or diffracted beam contains useful information about substrate characteristics and process parameters associated with the process being implemented relative to the substrate. Because the angular velocity at the central region near the axis is less than at radially outer areas, synchronization of the incident beam to interrogate the gratings and/or features at the central is facilitated. The measurement system 18 and/or the control system 22 thus can be programmed and/or configured to discern optical Be, properties of the substrate based on an analysis of the reflected and/or diffracted beam. The optical properties of the substrate can, in turn, be quantified to provide an indication of substrate physical properties, such as thickness of one or more layers being applied to and/or removed from the substrate, as well as defects associated therewith.

Figure 2:
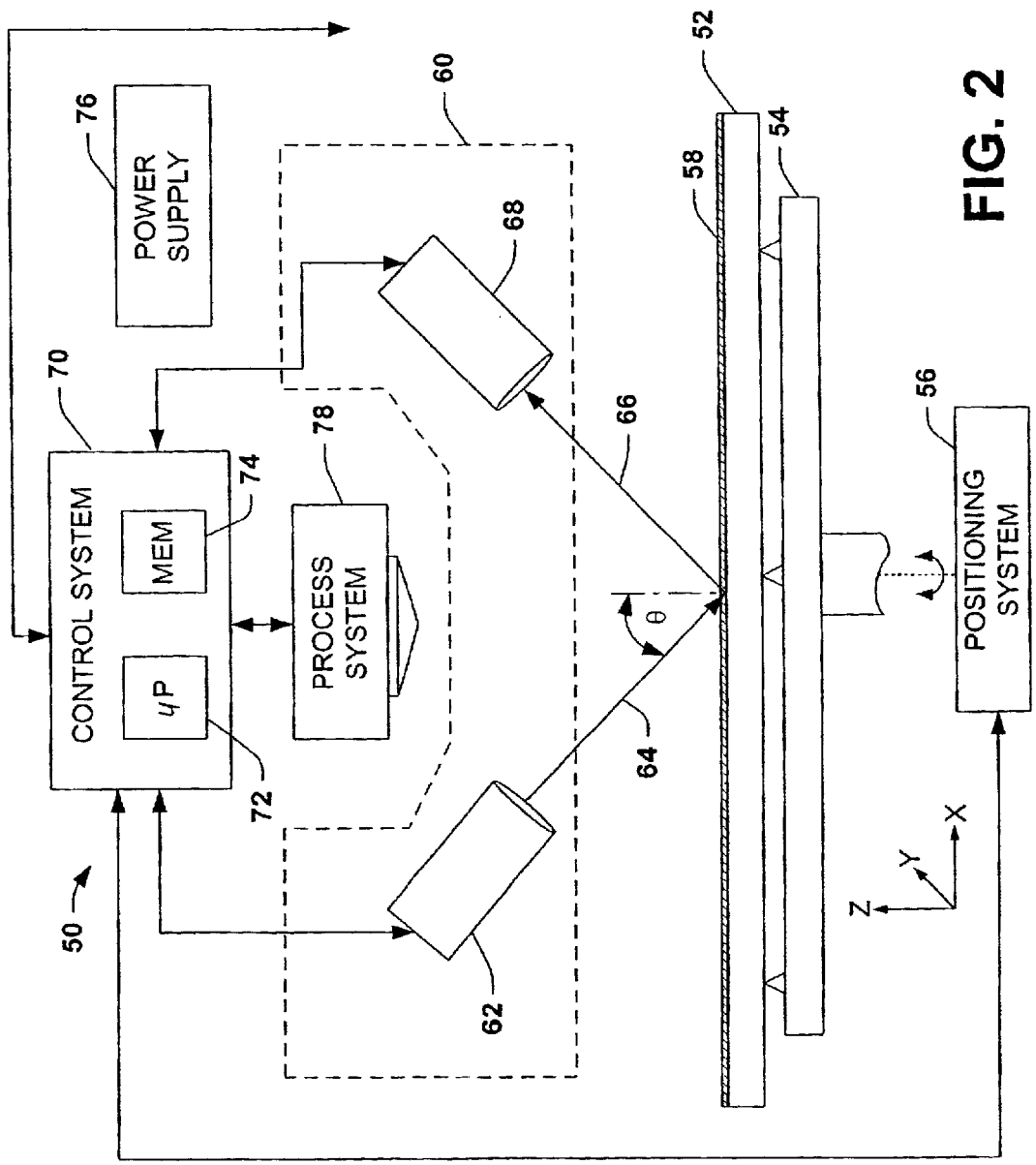
FIG. 2 is a schematic block diagram of an example of a monitoring system for measuring substrate characteristics in accordance with the present invention.

FIG. 2 illustrates another example of a system 50 for measuring characteristics of a substrate 52 in accordance with an aspect of the present invention. In this example, the substrate 52 is supported by a moveable support 54, such as a chuck. The support 54 is operatively connected to a positioning system 56. The positioning system 56 may be operable to move the support in one or more directions, such as the x, y, and/or z-directions. In addition, the positioning system 56 can include a suitable servomotor (not shown) for rotating the support 54 and the substrate 52 located thereon about the z-axis. The support 54 also can include a vacuum chuck operative to hold the substrate 52 at a fixed position relative to the support.

By way of further illustration, the substrate 52 includes one or more alignment markers, which are utilized to position the substrate at a predefined position relative to the upper surface of the support 54. The upper surface of the support 54 can include corresponding marks to facilitate such positioning. The positioning system 56 includes a position sensing device, such as one or more encoders (e.g., optical, magnetic, hall effect, etc.), which is employed to provide a signal having information indicative of the position of the support 54. The position information, can include rotary position about a central axis, as well as positions in mutually orthogonal axes along which the support 54 can move. Because the substrate 52 is at a known fixed position relative to the support 54, the absolute position of the substrate can be discerned from the encoder data.

Those skilled in the art will understand and appreciate other techniques that could be employed to discern the relative position of the substrate 52. For example, the substrate can include other alignment marks, reflectors, or apertures through the substrate to detect the relative angular position of substrate within the system 50.

The positioning system 56 controls the rate of rotation of the support 54, which may vary according to the process being implemented within the processing environment. For example, it may be desirable to rotate the support at a substantially fixed rate or it may be desirable to selectively adjust the rotation rate (e.g., accelerate or decelerate), such as at different stages of an associated fabrication process.

The rotation, for example, facilitates application and/or removal of a layer 58 relative to the substrate 52. By way of example, the layer 58 can be a film of a resist coating (e.g., being applied in spin coating system) or a layer being removed (e.g., in a stripper system), a layer of solvent material (e.g., in a developer). It will be understood and appreciated, however, that the present invention can be implemented as part of any system in which the substrate 52 rotates and when materials are applied to and/or removed from the substrate.

The system 50 also includes a measuring system 60 for measuring topographical features of the substrate 52 in accordance with an aspect of the present invention. By way of illustration, the measuring system 60 is a non-destructive measurement tool that includes a source of light 62, such as one or more optical emitters, for emitting an incident light beam 64 toward the substrate 52 at an incident angle, indicated at $\theta$ relative to a normal reference line. The light source 62 can be a frequency stabilized laser; however it will be appreciated by one skilled in the art that any laser or other light source (e.g., laser diode, or helium neon (HeNe) gas laser, halogen lamp, etc.) suitable for carrying out the present invention could be utilized.

At least a portion of the incident beam 64 is reflected and/or diffracted as a reflected beam 66. One or more optical detectors 68 receive the reflected and/or diffracted beam 66. The detector(s) 68 analyzes the characteristics of the reflected beam 66 and operative to discerning optical properties of the beam 66. As described below, the optical properties of the beam 66 describe optical characteristics of the substrate 52, which further correspond to substrate characteristics. The substrate characteristics, for example, can include feature characteristics, defects, and thickness of layers.

By way of example, the detector 68 can include a spectrometer or any instrument that capable of providing spectrally-resolved information concerning the reflected beam 66. The portion of the reflected beam 66 that enters the spectrometer for analysis is determined by the sample and its associated diffraction characteristics, the spatial extent of the reflected beam, properties of the detector 68, and any associated optical elements that might be used in conjunction with the detector.

In accordance with an aspect of the present invention, one or more gratings and/or features are located at a generally central region of the substrate 52, such as near the axis about which the substrate rotates. Because the features and/or gratings are located near the axis, the angular velocity at such radial position is less than at areas near the edge of the substrate 52 spaced radially outwardly from the axis. As a result of the diminished angular velocity at the central region, the synchronization of the incident beam with the angular orientation of the features and/or gratings is facilitated.

The detector 68 collects light reflected, and/or passed through one or more gratings and/or features. The measurement system 60 can extract information about the characteristics of the substrate 52 by comparing the phase and/or intensity of the incident beam 64 with phase and/or intensity signals of a complex reflected and/or diffracted light in the reflected beam 66. The intensity and/or the phase of the reflected and/or diffracted light 66 changes based on properties of the materials upon which the light is directed. Accordingly, the reflected and/or diffracted light 66 has optical properties corresponding to various properties of the substrate, such as, for example, chemical properties of the surface, the planarity of the surface, features on the surface, thicknesses of layers, voids in the surface, and the number and/or type of layers beneath the surface. In accordance with the present invention, the intensity and/or phase of the reflected and/or diffracted light also can be examined to discern to profiles of film thickness on the wafer being fabricated. The determined thickness measurements further can be employed as feedback during fabrication to adjust one or more operating parameters of an associated process.

Examples of techniques that may be utilized in accordance with an aspect of the present invention include optical interference, ellipsometry, reflectometry, capacitance, and use of an associated color chart. Microprocessor controlled scatterometry or optical interference (e.g., microspectrophotometry) and spectroscopic ellipsometry are types of non-destructive optical measurement techniques that could be utilized in accordance with an aspect of the present invention.

A control system 70 is operatively coupled to the positioning system 56 and to the measuring system 60, including the light source 62 and the detector 68. The control system 70 receives an indication of the optical characteristics of the beam 66 from the detector 68 as well as an indication of the position and/or velocity from the positioning system 56. The control system 70 is programmed and/or configured to determine substrate characteristics based on the information provided by from the associated system components.

The control system 70 includes a processor 72 and memory 74. The processor 72 is programmed and/or configured to control and operate the various components within system 50 in order to carry out the various functions described herein. The processor 72 can be any of a plurality of processors, including commercially available and/or proprietary processors. The manner in which the processor 72 can be programmed to carry out the functions relating to the present invention will be readily apparent to those having ordinary skill in the art based on the description provided herein.

The memory 74 stores program code executed by the processor 72 for carrying out operating functions of the system 50. The memory 74 also serves as a storage medium for temporarily storing information, such as rotation/position information, wafer coordinate tables, scatterometry information, and other data that may be employed in carrying out the present invention.

A power supply 76 provides operating power to the system 50. Any suitable power supply (e.g., battery, line power) 76 may be utilized to carry out the present invention.

By way of illustration, the control system 70 provides control signals to the measuring system 60 and to the positioning system 56 to synchronize their operation in accordance with an aspect of the present invention. In particular, the positioning system 56 and light source 62 can be controlled such that the incident beam 64 is emitted in synchronization with the rotation (e.g angular orientation) of the substrate 52. Because the emission of the incident beam 64 and the rotation of the substrate 52 cooperate in this manner, the beam is able to selectively interrogate one or more selected centrally located gratings and/or features when the substrate is at a desired angular orientation relative to the incident beam. The incident beam 64 thus can interrogate the gratings and/or features from a desired predetermined angle to facilitate the analysis of the reflected and/or diffracted light 66. As a result, errors associated with the measurements due to movement (e.g., rotation) of the substrate 52 during measuring are mitigated.

By way of further illustration, the system 50 may be implemented within a fabrication process. A process system 78 can be provided to apply material onto and/or remove material from the substrate 52, such as resist coating, a developing solution, an etchant, stripping, cleaning, etc. The process system 78 is operatively coupled to the control system 70 for receiving control information and/or providing feedback indicative of process conditions. In addition, the control system 70 can adjust operating characteristics of the process system 78 based on the measurement data and/or the rotation data from the measuring system 60 and the positioning system 56, respectively. In particular, the control system 70 can control operation of the measuring system 60, the positioning system 56, the application system 78, and/or other operating characteristics (e.g., substrate alignment, temperature, etc.) so as to improve the efficiency and/or accuracy of the various process steps being implemented. As a result, application (or removal) of a uniform and desired amount of material on the substrate can be facilitated.

By way of illustration, scatterometry can be employed to extract information about a surface of a substrate upon which an incident light 64 has been directed. One or more gratings may be located near a central region of a substrate. Such gratings can be formed on the substrate, for example, at the same stage in fabrication when alignment markers are formed thereon, such as by etching.

Figure 3:
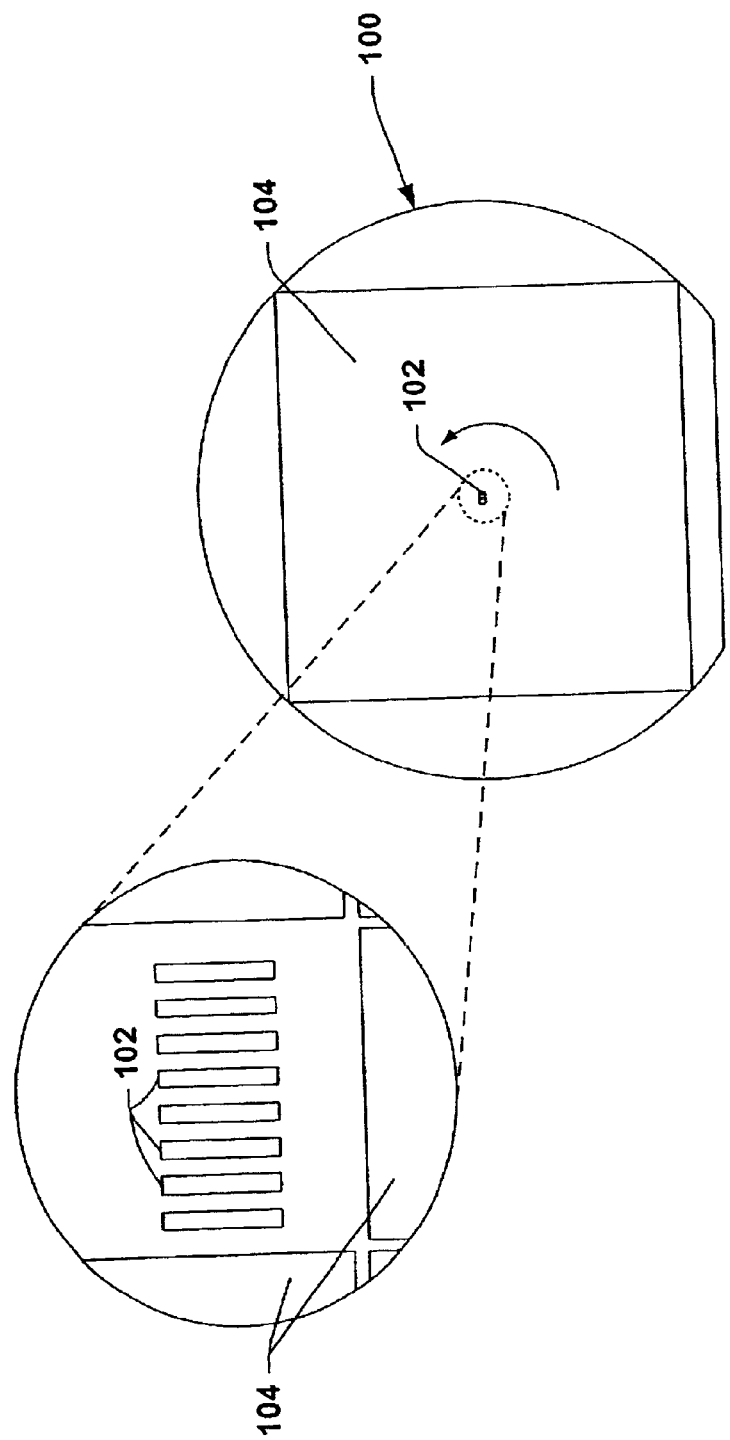
FIG. 3 is a plan view of a substrate located on a rotating support in accordance with an aspect of the present invention.

Referring to FIG. 3, an example of a substrate (e.g, a wafer) 100 such as may be rotating on a support within a process chamber having gratings 102 is illustrated for use in accordance with an aspect of the present invention. As shown in FIG. 3, the gratings 102 are located near a central region of the substrate 100 to facilitate inspection and/or measurements of the substrate. The gratings can be located between production regions 104 of the substrate 100 so as to maximize real estate associated with the substrate being manufactured. The particular grating illustrated in FIG. 3 is a series of elongated parallel marks, which can be implemented as raised portions in the substrate or as troughs, such as etched into the substrate. It is to be appreciated that more complex (e.g., nonlinear) grating patterns and/or substrate features (e.g., lines, connectors, etc) also could be used in accordance with an aspect of the present invention.

Figure 4:
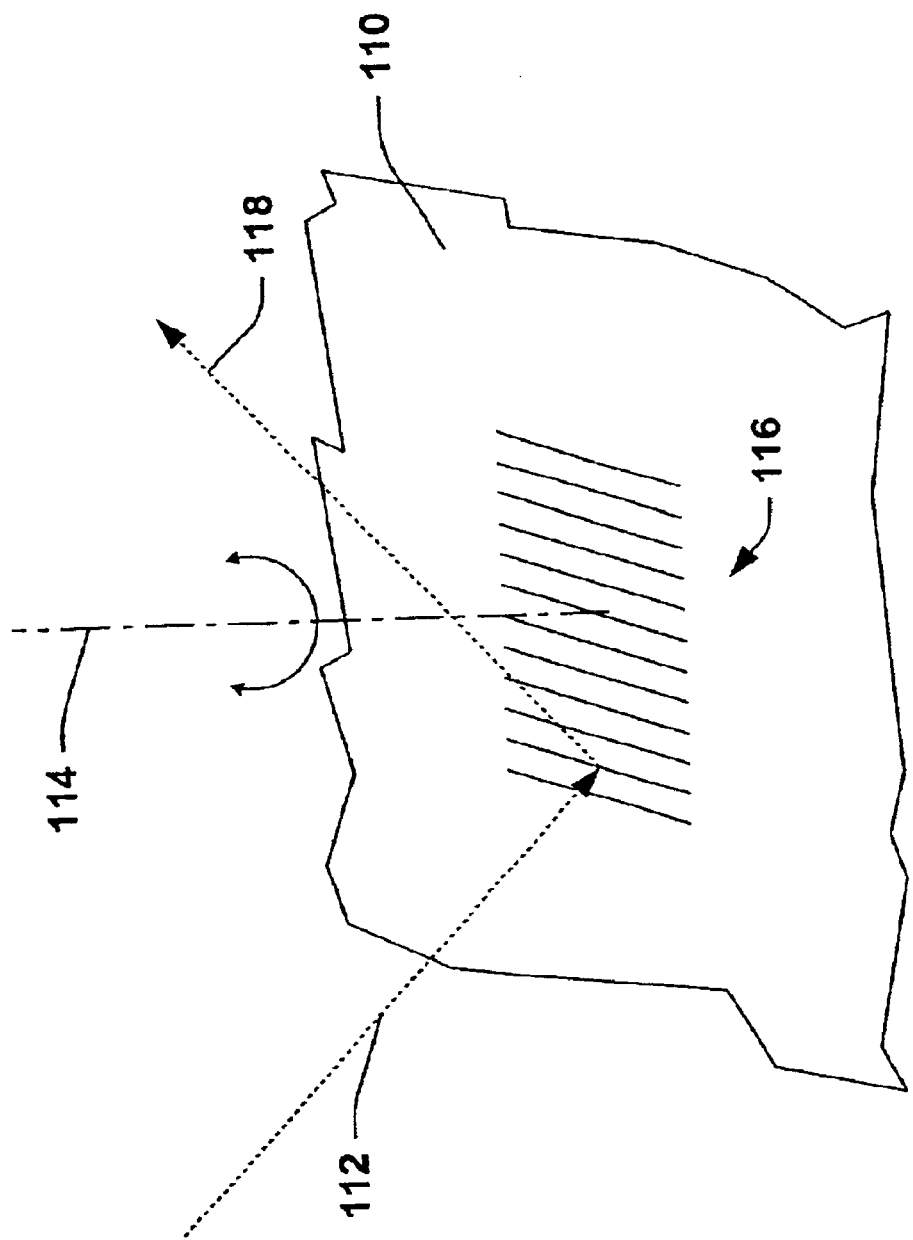
FIG. 4 is an isometric view of part of a substrate illustrating gratings being interrogated in accordance with an aspect of the present invention.

FIG. 4 illustrates a central part of a substrate 110 being interrogated by an incident beam 112 in accordance with an aspect of the present invention. In particular, the substrate 110 is rotating about an axis 114. A grating pattern 116 is located near the part of the substrate 110 through which the axis 114 extends. The incident beam 112 strikes the substrate 110 at the grating pattern 116 to produce reflected and/or diffracted light, indicated at 118. As mentioned above, the reflected and/or diffracted light 118 has optical characteristics indicative of various substrate characteristics.

In accordance with an aspect of the present invention, because the angular orientation of the gratings 116 relative to the substrate is known, the control system 70 (FIG. 2) can control the light source to emit the incident beam 112 at a desired angle relative to the grating pattern, such as shown in FIG. 4. Thus, as the substrate 110 rotates the beam 112 can be turned ON and OFF, such that the beam is emitted when the grating pattern 116 is appropriately aligned with the incident beam. For example, the incident beam 112 can be controlled according to a strobe or pulsed technique, so that the gratings 116 are interrogated when properly aligned relative to the incident beam. As a result, the incident beam 112 can be emitted in synchronization with the angular alignment of the grating pattern 116 to facilitate collection of useful information about the substrate 110 and the process being implemented relative to the substrate.

By way of particular illustration and with reference back to FIG. 2, the measurement system 50 could be implemented as a broadband scatterometry system. In general, scatterometry is a technique for extracting information about a surface upon which an incident light has been directed. Information concerning properties including, but not limited to, dishing, erosion, profile, thickness of thin films and critical dimensions of features present on a surface such as a wafer can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the substrate, and the number and/or type of layers beneath the surface. In the present invention, the intensity and/or phase of the reflected and/or diffracted light may be examined as it relates to profiles of film thickness and/or gratings on the wafer being fabricated. The determined thickness measurements further can be employed as feedback during fabrication to adjust one or more operating parameters of a process, such as application and/or removal of materials provided by the process system 78.

In another aspect of the invention a reflectometry technique can be employed to determine characteristics (e.g., film thickness, critical dimensions, defects, etc.) of a moving substrate. With a reflectometry technique, the light source 62 emits the beam of light 64 that is supplied at a fixed incident angle θ (e.g., about 90 degrees) relative to surface of the substrate 52. The spectral reflectivity of the substrate surface is modulated by optical interference. The effect of the interference on the measured spectrum is a function of the refractive indices of the substrate surface 58 receiving the incident light 64. For example, if the wavelength of the incident beam 64 is varied, such as between a wavelength in the range of about 100–800 nm, and if the dispersion components of the refractive indices are known over the wavelength range, the thickness of the oxidized portion can be found using a Fourier transform technique. Other transformation techniques can be employed to carry out the present invention. The light source 62, for example, can be a frequency-stabilized laser; however, it will be appreciated that any laser or other light source (e.g., laser diode or helium neon (HeNe) gas laser) suitable for carrying out the present invention may be employed.

The intensity of the reflected light beam 66 can be measured as a function of its wavelength, with a minimal intensity being used to calculate various characteristics of the substrate 52, including film thickness. In accordance with an aspect of the present invention, the measurement system 60 controls the light source 62 and/or the detector 68 so as to selectively interrogate a given grating or different gratings at different locations on the substrate. The measurement system 60 and/or control system 70 thus can derive an indication of the optical properties associated with the central part of the substrate with which the beam 64 interacts. The measurement system 60, in turn, can provide an indication of the measured optical properties to the associated control system 70. The control system 70 further can control the measurement system 60 and/or the positioning system 56 to synchronize their operation to mitigate errors that could be associated with measuring characteristics of the moving substrate 52.

By way of further example, when the measurement system 60 is implemented as part of a reflectivity system, it can employ pre-selected values for the index of refraction to facilitate calculating the thickness of the layers and other characteristics of the substrate based on the measure properties of the reflected beam relative to the incident beam. The information provided by the measurement system 60, for example, may include an indication of the thickness, such as based on analysis of the magnitude and phase of the incident beam 64 and the reflected and/or diffracted light beam 66. Alternatively, the measurement system 60 can provide raw data to the associated control system 70, which may employ such data to derive an indication of desired substrate characteristics.

Figure 5:
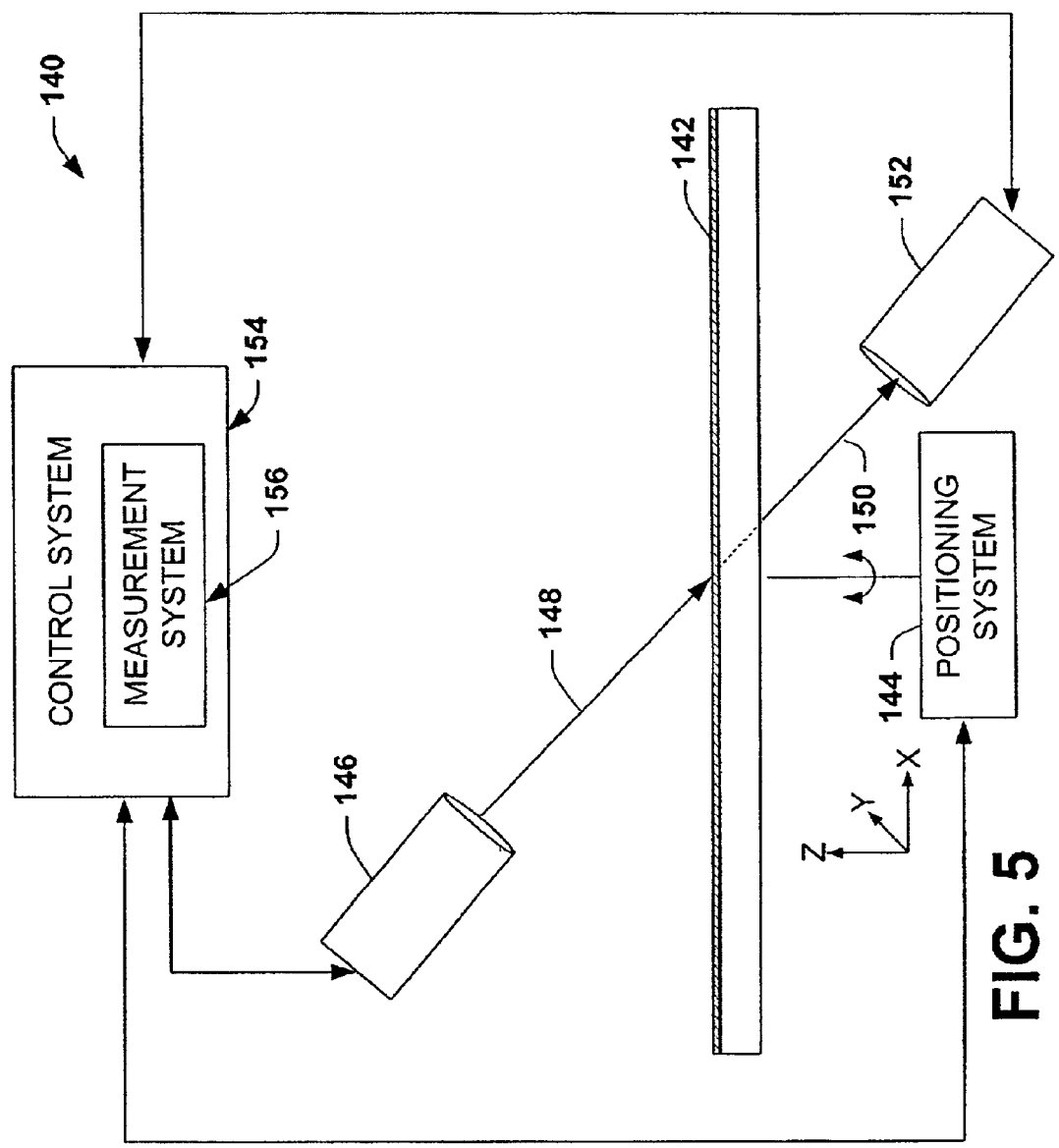
FIG. 5 is a schematic block diagram of part of a monitoring system, illustrating another example of a system for measuring substrate characteristics in accordance with the present invention.

FIG. 5 illustrates an arrangement 140 that is similar in function to that illustrated in FIG. 2, and which accommodates substrates 142 that are partially or fully transparent. The substrate 142 is supported for rotation by a positioning system 144. In this example, a light source 146 provides an incident beam 148, at least a substantial portion of which is transmitted through the substrate 142. A diffracted and/or refracted beam 150 exits the side of the substrate 142 opposite to that of the incident beam 148. At least a portion of the diffracted beam 150 enters a spectrometer 152, which may be processed using known scatterometry techniques as described herein.

By way of example, a control system 154, which is operatively coupled to the light source 146, the spectrometer 152, and the positioning system 144, is programmed and/or configured to control operation of such components. In particular, the control system 154 includes a measurement component 156 programmed and/or configured to controls operation of the light source 146 and the spectrometer 152. As indicated below, the measurement component 156 also is programmed to determine characteristics of the substrate 142 based on optical data obtained by the spectrometer 152 based on the beam 150.

The control system 154 also is programmed and/or configured to control the light source 146 to emit the incident beam 148 as a function of angular orientation of the substrate 142 so as to facilitate measurement of the substrate characteristics. For example, the control system 154 can employ position/rotation information from the positioning system 144 to control the light source 108 to intermittently provide a pulsed incident beam 148, such as according to a strobe technique.

In particular aspect of the present invention, a grating pattern is provided at a central region of the substrate 142 near an axis about which the substrate rotates. The grating pattern, for example, includes a series of light substantially parallel grating lines. Thus, to facilitate collection of useful information about the substrate, the control system 154 controls the light source 146 to emit the incident beam 148 according to a strobe technique to interrogate the gratings when at a desired angular orientation (e.g., generally normal) relative to the incident beam (See, e.g., FIG. 4). As a result, the pulsed incident beam(s) 148 can selectively interrogate gratings and/or features of the substrate 142 at the central region while the substrate is rotated by the positioning system 144.

Alternatively or additionally, the control system 154 can control operation of the positioning system 144 based on a predetermined pulsed emission pattern for the incident beam 148 provided by the light source 146. In this way, sensed or otherwise known operating parameters of the light source 146, the detector 152, and/or the positioning system 144 can be utilized to synchronize operation of the measuring and positioning systems.

Figure 6:
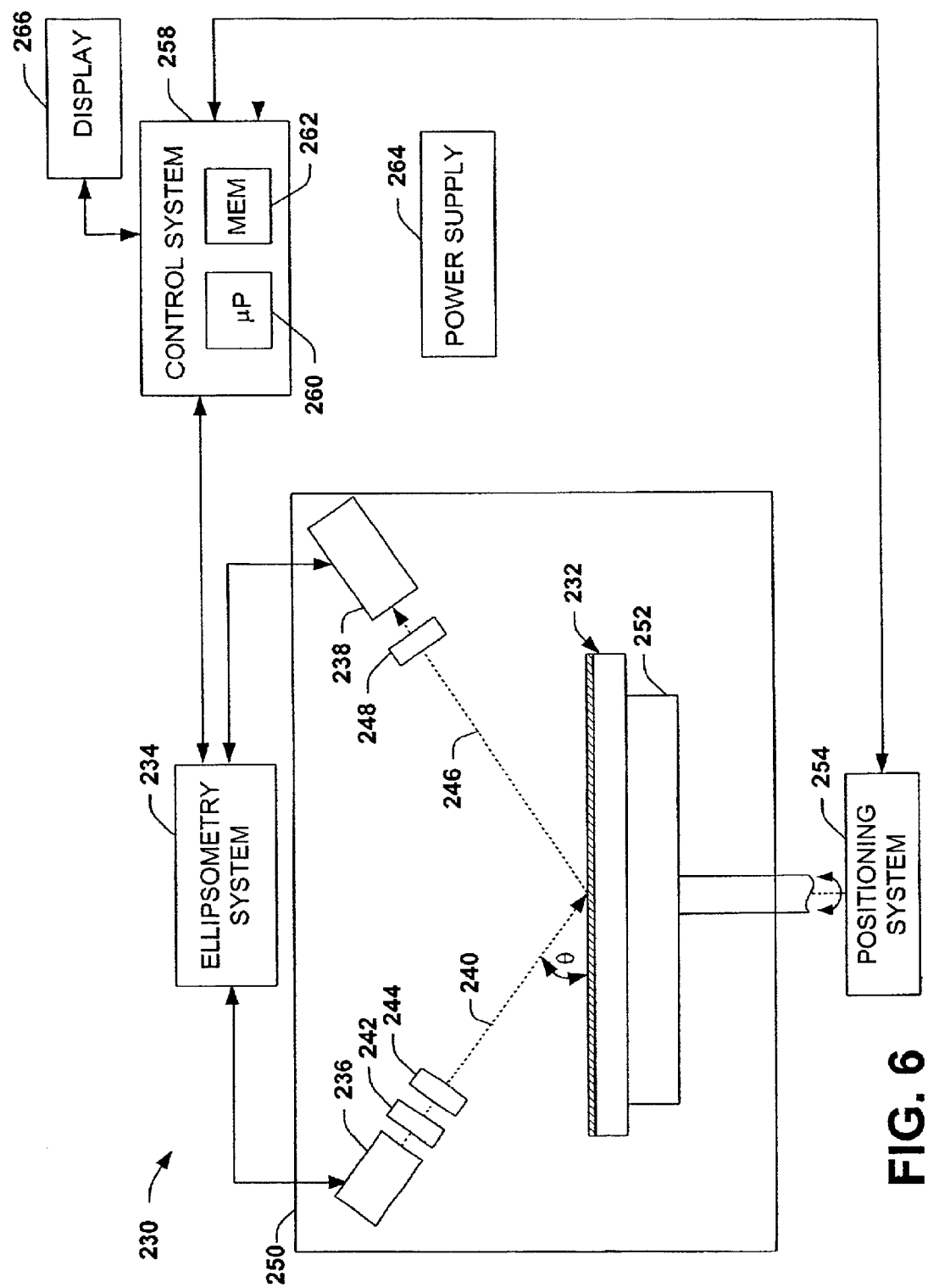
FIG. 6 is a schematic block diagram of part of a monitoring system, illustrating yet another example of a system for measuring substrate characteristics in accordance with the present invention.

FIG. 6 illustrates an example of a measurement system 230 that can be implemented to measure characteristics of a substrate 232 in accordance with an aspect of the present invention. The measurement system 230 includes a spectroscopic ellipsometry system 234 coupled to a light source 236 and an optical detector 238. The light source 236 is a broadband light source, such as a Xe Arc lamp or the like.

The light source 236 produces a spectrum of polychromatic light over a predetermined wavelength range of interest (e.g., about 100–800 nm). The light source provides a light beam 240 through an optical network 242 that includes one or more lenses and/or mirrors. The beam 240 then interacts with a polarizer 244 to create a known polarization state for the beam. Various polarizers can be employed to carry out the present invention. The azimuth angle of the polarizer is oriented so that the plane of the electric vector associated with the linearly polarized beam exiting from the polarizer 244 is at a known angle θ relative to the plane of incidence defined by the propagation direction of the beam and a normal to the exposed surface of the substrate 232.

By way of illustration, the azimuth angle is selected, so that the reflected intensities of P and S polarized components are approximately balanced (e.g., 25–50°). At least a portion of the beam is reflected, indicated at 246, and received at the optical detector 238. The beam 246 will have a mixed linear and circular polarization state after interacting with the substrate 232. The reflected beam 246 will then pass through an analyzer 248, which operates to mix the polarization states incident on it. Either the polarizer 244 or the analyzer 248 is rotated, so that the detector 238 can characterize the beam 246. The beam 246 then enters the detector 238 which measures the intensity of the different wavelengths of light through the wavelength range of interest that pass through the analyzer 248. The detector 238 or the ellipsometry system 234 then determines, for example, the tan(PSI) and the cos(Delta) and utilizes this determination in relating a signature to the desired characteristics of the substrate 232 being determined.

In accordance with a particular aspect of the present invention, the ellipsometry system collects measurement data at a central region of the surface of the layer being formed. Specifically, the light source is controlled to selectively interrogate gratings and/or features located at the central region of the substrate based on the determined angular orientation of the substrate relative to the light source 236. The measurements are then employed to determine substrate characteristics, such as uniformity of the a thin film being applied to or removed from the substrate 232 Moreover, upon determining a generally non-uniform layer, selected fabrication process parameters may be adjusted to facilitate uniform layer formation.

The system 230 includes a process chamber 250 that includes a support, such as a stage (or chuck) 252 operative to support the substrate 232. A positioning system 254 is operatively connected to the support 252 for positioning the stage at a desired position within the chamber 250. The positioning system 254 further can move the stage 252 and the substrate 232 supported thereon in one or more directions, such as rotationally and along one or more orthogonal axes. It is to be appreciated that wafer positioning systems are rapidly evolving and that any such system can be employed in accordance with an aspect of the present invention.

The movement facilitates application of chemicals, such as may be applied as part of a deposition process, a coating process, etching process. For example, deposition processes that can be utilized, in accordance with an aspect of the present invention, include Low Pressure CVD (LPCVD), Plasma Enhanced CVD (PECVD), and Rapid Thermal CVD (RTCVD). It is to be appreciated, however, that the present invention is applicable to other types of thin film formation, such as other deposition techniques (e.g., Physical Vapor Deposition (PVD), Metal Organic Chemical Vapor Deposition (MOCVD), Pulsed Laser Deposition (PLD)) and film growth techniques. The present invention further is applicable to various processes in which one or more layers of a substrate are removed, such as when cleaning or stripping materials from a surface of the substrate 232.

The ellipsometry system 234 is operative to measure characteristics of the substrate 232 in-situ, in accordance with an aspect of the present invention. In the example illustrated in FIG. 6, the ellipsometry system 234 is operative to measure desired characteristics of the substrate, including critical dimensions, film thickness, film composition, defects, voids, etc.

For the example of optical interference, the intensity of light over a selected wavelength varies as a function of layer thickness. For spectroscopic ellipsometry, thickness varies based on the state of polarization of light reflected from the film, which is functionally related to the index of refraction of the material reflecting the beam 240.

By way of further illustration, the substrate 232 has gratings formed thereon at a central region near its rotational axis, such as may be formed concurrently with alignment markings on the substrate. The gratings, for example, may range from about 10×10 μm to about 100×100 μm, such as depending on the type of measurement tool being employed. The ellipsometry system, in turn, may employ a scatterometry technique using spectroscopic ellipsometry to measure thickness of films being applied at the gratings. Thus, the ellipsometry system 234 may measure properties of the wafer near the axis about which the substrate rotates.

Using a spectroscopic ellipsometry technique, for example, desired information concerning layer thickness can be extracted by comparing the phase and/or intensity (magnitude) of the light directed onto the surface with phase and/or intensity signals of complex reflected and/or diffracted light resulting from the incident light reflecting from and/or diffracting through the surface upon which the incident light was directed. The intensity and/or the phase of the reflected and/or diffracted light will change based on properties of the surface upon which the light is directed, including layer thickness, defects, voids, etc.

Different combinations of the above-mentioned properties will have different effects on the phase and/or intensity of the incident light resulting in substantially unique intensity/phase signatures in the complex reflected and/or diffracted light. The spectroscopic ellipsometry system 234 provides information indicative of the measured properties to a control system 258. Such information may be the raw phase and intensity information. Alternatively or additionally, the spectroscopic ellipsometry system 234 can be programmed and/or configured to derive an indication of detected substrate characteristics (e.g., layer thickness, defects, critical dimensions, etc.) based on the measured optical properties and provide the control system 258 with a signal indicative of the detected substrate characteristics. The phase and intensity of the reflected light 246 further can be measured and plotted.

In accordance with an aspect of the present invention, the positioning system 254 also is coupled to the control system 258. The positioning system 254 provides a signal indicative of the position and/or velocity of the stage 252. The control system 258 thus can determine the absolute position (e.g., angular orientation) of the substrate 232 within the process chamber 250 relative to the light source 236 and detector 238. Such determination is enabled because the position of the substrate relative to the stage is known.

The control system 258 also is programmed and/or configured to control the light source 236 to emit the incident beam 240 as a pulsed beam, such as according to a strobe technique. For example, the control system controls the source 236 to pulse the beam 240 so as to selectively interrogate a grating pattern of the substrate 232 located at a central region of the substrate as the substrate is rotated by the positioning system. Because the gratings are near a central location about which the substrate is rotating, such gratings experience a reduced angular velocity relative to the light source if compared relative to locations spaced radially outwardly from the axis of the rotating substrate. Consequently, interrogation of the central gratings and/or features of the substrate is facilitated the closer the gratings are located relative to the center.

The measurements made at the central location can be employed to determine uniformity layers being formed across the surface of substrate 232 and or provide an indication of movement of materials from a central region onto which such materials are applied. Moreover, upon determining unexpected characteristics of the substrate 232, such as a generally non-uniform layer or defects in the layer being formed, selected fabrication process parameters can be adjusted to facilitate desired processing.

In order to determine layer thickness, for example, measured signal characteristics are employed to generate a signature corresponding to the Tan(PSI) over the broadband frequency range and a signature corresponding to the Cos (Delta) over the broadband frequency range. The generated signatures may be compared with a signal (signature) library of intensity/phase signatures to determine the desired characteristics of the moving substrate. Such substantially unique phase/intensity signatures are produced by light reflected from and/or refracted by different surfaces due, at least in part, to the complex index of refraction of the surface onto which the light is directed.

The signal (signature) library can be constructed from observed intensity/phase signatures and/or signatures generated by modeling and simulation. By way of illustration, when exposed to a first incident light of known intensity, wavelength and phase, a first feature on a wafer can generate a first component of a phase/intensity signature. Similarly, when exposed to the first incident light of known intensity, wavelength and phase, a second feature on a wafer can generate a second component of a phase/intensity signature. The components can be determined over a broadband range of wavelengths and aggregated to form a signature. For example, a particular type of thin film having a first thickness may generate a first signature while the same type of film having a different thickness may generate a second signature, which is different from the first signature.

Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing, for example, numerous phase/intensity signatures. Thus, when the phase/intensity signals are received from ellipsometry detecting components, the phase/intensity signals can be pattern matched, for example, to the library of signals to determine whether the signals correspond to a stored signature. Interpolation between the two closest matching signatures further may be employed to discern a more accurate indication of thickness from the signatures in the signature library. Alternatively, artificial intelligence techniques can be employed to calculate desired parameters of the wafer under test based on the detected optical properties.

The control system 258 also includes a processor 260, such as a microprocessor or CPU, coupled to a memory 262. The processor 260 receives measured data from the spectroscopic ellipsometry system 234. As mentioned above, the control system 258 is programmed and/or configured to control and operate the various components within the measurement system 230 in order to carry out the various functions described herein.

The processor 260 can be any of a plurality of commercially available and/or proprietary processors. The manner in which the processor 260 can be programmed to carry out the functions relating to the present invention will be readily apparent to those having ordinary skill in the art based on the description provided herein.

The memory 262 serves to store program code executed by the processor 260 for carrying out operating functions of the system as described herein. The memory 262 may include read only memory (ROM) and random access memory (RAM). The ROM contains among other code the Basic Input-Output System (BIOS), which controls the basic hardware operations of the system 230. The RAM is the main memory into which the operating system and application programs are loaded. The memory 262 also serves as a storage medium for temporarily storing information such as temperature, temperature tables, position coordinate tables, interferometry information, thickness tables, and algorithms that may be employed in carrying out the present invention. The memory 262 also can hold patterns against which observed data can be compared as well as information concerning grating sizes, grating shapes, ellipsometry information, achieved profiles, desired profiles and other data that may be employed in carrying out the present invention. For mass data storage, the memory 262 can include a hard disk drive.

A power supply 264 provides operating power to the system 230. Any suitable power supply (e.g., battery, line power) may be employed to carry out the present invention. The system further may include a display 266 operatively coupled to the control system 258 for displaying a representation (e.g., graphical and/or text) of one or more process conditions, such as layer thickness, temperature, gas flow rates, etc. The display 266 further may show a graphical and/or textual representation of the measured optical properties (e.g. refraction index and absorption constant) at various locations along the surface of the substrate.

As a result, the system 230 provides for monitoring process conditions, including layer thickness, defects, and other sensed process-related conditions, associated with the layer formation process within the chamber 250. The monitored conditions provide data based on which the control system 258 can implement feedback process control so as to form a layer having a desired thickness, such as a uniform thickness across the substrate based on the thickness measurements made at the central region interrogated by the measurement system in accordance with an aspect of the present invention.

Figure 7:
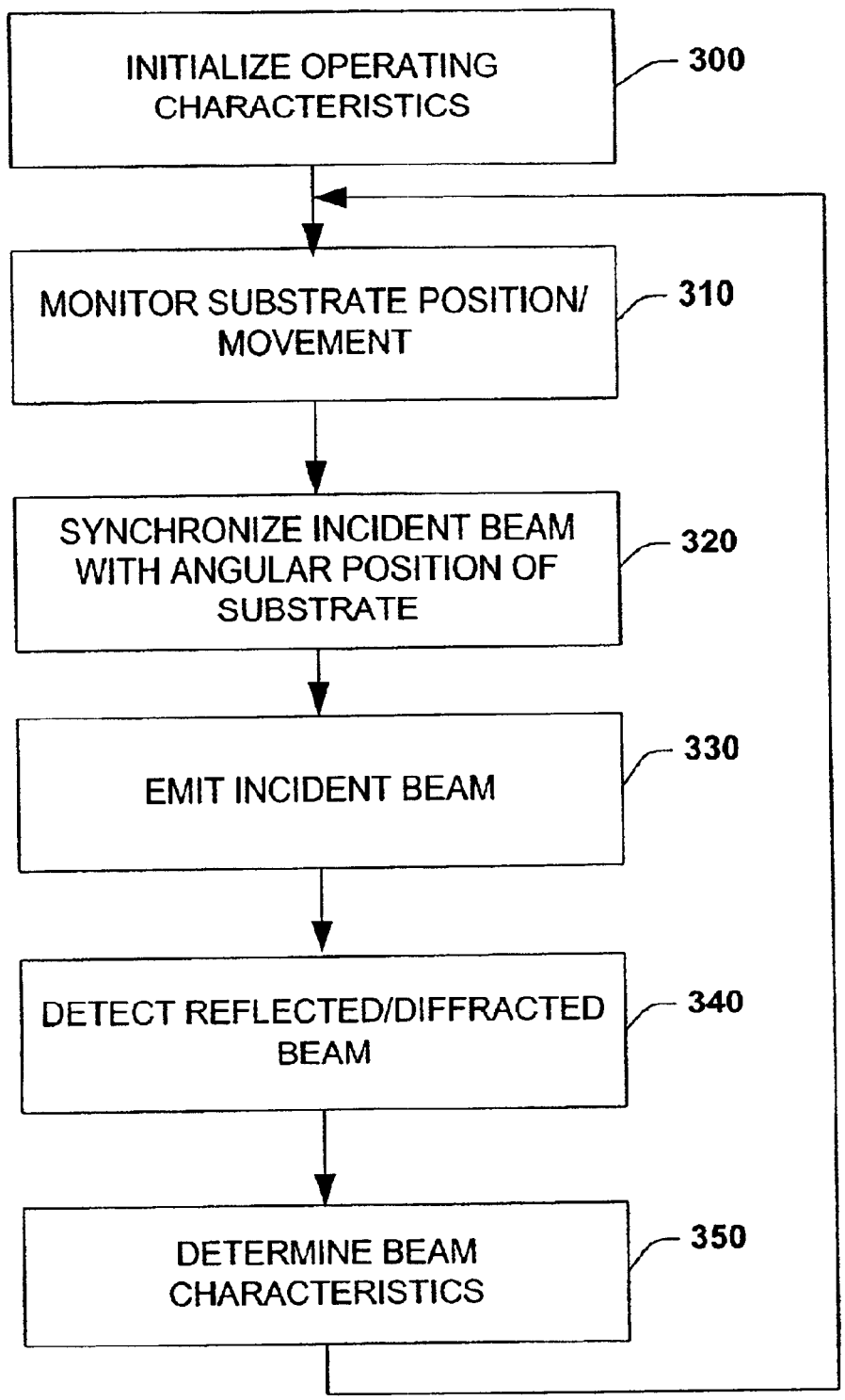
FIG. 7 is a flow diagram illustrating an example of a methodology for monitoring substrate characteristics of a substrate in accordance with the present invention.
Figure 8:
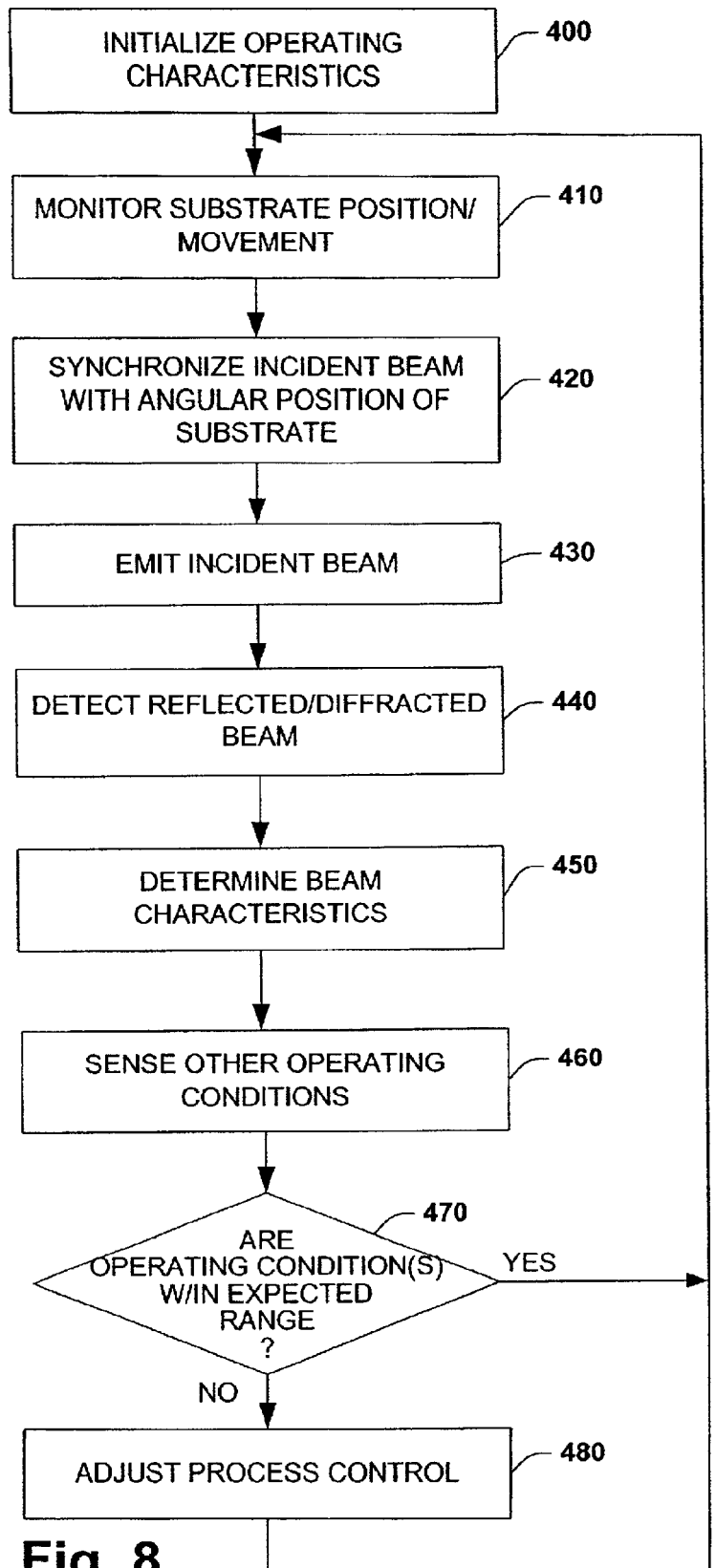
FIG. 8 is a flow diagram illustrating another example of a methodology for monitoring substrate characteristics and implementing process control in accordance with the present invention.

In view of the exemplary systems shown and described above, a methodology, which may be implemented in accordance with the present invention, will be better appreciated with reference to the flow diagrams of FIGS. 7 and 8. While, for purposes of simplicity of explanation, the methodologies of FIGS. 7 and 8 are shown and described as executing serially, it is to be understood and appreciated that the present invention is not limited by the illustrated order, as some aspects can, in accordance with the present invention, occur in different orders and/or concurrently with other aspects from that shown and described herein. Moreover, not all illustrated functionality may be required to implement a methodology in accordance with the present invention.

Turning to FIG. 7, the methodology begins at 300 in which operating characteristics are initialized to their starting values. This may include, for example, controlling rotation of a support on which a substrate is positioned and/or setting initial optical parameters of an incident beam for measuring topographical characteristics of the substrate in accordance with an aspect of the present invention.

Next, at 310, the substrate position and/or movement (e.g., rotation) are monitored. The position and/or rotation can be measured using an encoder or based on sensed operating characteristics of a motor, which provides for the rotation of the substrate support. Alternatively or additionally, other position detection systems could be employed to determine when the substrate and, more specifically, the gratings, are oriented at a desired angular position relative to the incident beam. From 310, the process proceeds to 320.

At 320, emission of the incident beam is synchronized with the movement of the substrate. By way of example, the light source is activated intermittently (e.g., pulsed according to a strobe technique) based on the determined angular orientation of the substrate (310). Specifically, the light source is controlled so as to intermittently emit the incident beam onto centrally located diffraction grating(s) when such gratings have a desired angular orientation relative to the incident beam. Because the gratings and/or features being interrogated are near the rotation axis of the substrate, and therefore have a smaller angular velocity relative to parts of the substrate spaced from the central region, the interrogation of the gratings is facilitated.

Next, at 330, an incident beam is emitted. The incident beam, for example, is intermittently emitted as a pulsed beam, with the pulses being synchronized with angular orientation of the substrate to facilitate measuring substrates characteristics. In accordance with an aspect of the present invention, the beam is emitted so as to interrogate gratings and/or features at a central location of the substrate, such as when the gratings are at a desired angular orientation relative to the incident beam. For example, when the gratings are substantially parallel lines, it may be desirable to emit the beam when the lines are oriented transverse relative to the incident beam so as to facilitate diffraction when the beam strikes the gratings. From 330, the process proceeds to 340.

At 340, a diffracted and/or reflected beam produced from the incident beam interacting with the substrate is detected. The reflected and/or diffracted beam, for example, is collected by a spectrometer or other optical detection device capable of detecting properties of the reflected and/or diffracted beam. Because the incident beam captures the gratings at a desired angle (e.g., generally normal to the incident beam), the reflected and/or diffracted beam contain useful, quantifiable information indicative of optical characteristics of the substrate.

At 350, the optical properties and characteristics of the reflected and/or diffracted beam are determined. The optical characteristics, for example, can include wavelength(s) and intensity of light, refraction indices, polarization state, etc. of the reflected and/or diffracted beam. The optical characteristics may be employed to derive an indication of process parameters, such as by determining whether the diffraction characteristics are within an expected range of values based on statistically determined calibration data. The calibration data, for example, can be stored as a signature library determined from simulation and/or model generation techniques. The determination further can be facilitated by employing, for example, neural nets, correlation techniques, pattern recognition techniques, or other artificial intelligence.

From 350, the process returns to 320 where the foregoing methodology is repeated, such as for a time period commensurate with rotation of the substrate and it is desirable to monitor substrate characteristics. As a result, surface properties of the substrate (e.g., feature dimensions, thickness of one or more layers, defects, etc.) can be determined even while the substrate is rotating in accordance with an aspect of the present invention. The determined surface properties can, in turn, be utilized to adjust associated processing steps to afford greater efficiency and accuracy.

FIG. 8 is a flow diagram illustrating another methodology for carrying out the present invention. The process begins at 400 in which operating characteristics are initialized to their starting values. This may include, for example, controlling rotation of a support on which a substrate is positioned, setting initial optical parameters (e g., intensity and wavelength(s)) of an incident beam, and/or controlling initial process parameters associated with fabrication of the substrate in accordance with an aspect of the present invention.

Next, at 410, the substrate position and/or movement (e.g., rotation) are monitored. The position and/or rotation information may be provided to a control system associated with the fabrication process in which the methodology of FIG. 8 is being implemented. From 410, the process proceeds to 420, in which emission of an incident beam is synchronized with the angular orientation and/or movement of the substrate. The angular orientation of the substrate, for example, can be determined from encoder data provided by a positioning system that drives rotational movement of the substrate and/or from monitoring the position of alignment features printed on or formed through the substrate. By synchronizing the incident beam with the position and/or rotation of the substrate, the incident beam can selectively interrogate a desired part of the substrate. The selective interrogation affords greater accuracy in measuring substrate characteristics as described herein.

At 430, an incident beam is emitted. The incident beam, for example, is emitted as a pulsed beam(s) near a central rotational axis of the substrate. The pulses are synchronized with rotation of the substrate to facilitate interrogating gratings and/or other features located at a central region of the substrate. Because the gratings and/or other features being interrogated are located near an axis about which the substrate rotates, the angular velocity relative to the source of the incident beam is mitigated. As a result, the synchronization (420) is facilitated and overall accuracy of the measurements can be improved. The incident beam is reflected and/or diffracted to produce a beam having characteristics indicative of substrate properties illuminated by the incident beam. From 430, the process proceeds to 440.

At 440, the reflected and/or diffracted beam is detected, such as using a spectrometer, although other optical detection techniques capable of detecting the reflected and/or diffracted beam could be used. Next, at 450, optical characteristics of the detected reflected and/or diffracted beam, such as intensity of one or more wavelengths of the detected light, phase characteristics, refractive indices, polarization state, etc., are determined. The optical characteristics may be employed to derive an indication of process and substrate parameters, such as described above with respect to FIG. 7.

From 450, the process proceeds to 460 in which other operating conditions associated with the process are sensed. The other operating conditions, for example, may include temperature, pressure, rates at which gases are applied into the process chamber, the amount and/or rate at which other materials (e.g., films, solutions) are applied to the substrate, etc. The methodology then proceeds to 470.

At 470, a determination is made as to whether the operating conditions are within an expected range. If the operating conditions are within an expected range of parameters, the process returns to 410 and the foregoing methodology is repeated. If the determination at 470 is negative, indicating that operating conditions are outside the expected range, the process proceeds to 480. At 480, process control is adjusted, which may include adjusting one or more process parameters, such as the rotation rate of the substrate, application of materials onto the substrate, temperature and/or pressure of the environment in which the substrate is being processed, measurement and/or inspection parameters, etc. The type and level of control implemented can vary according to particular application in which the methodology is being utilized. It is to be appreciated that the control also can vary according to the stage of the fabrication process. The desired amount of adjustment to one or more operating parameters of the process further may be based on the sensed operating conditions (410, 440, 460), such as may include the substrate characteristics (e.g., physical or chemical properties based on the detected light beam), the position/rotation of the substrate, temperature, application rate(s) of materials. Those skilled in the art will understand and appreciate other process parameters that one may desire to monitor and/or adjust according to various stages of the fabrication process in which the present invention can be implemented, all of which are contemplated by the present invention.

From 480, the present iteration ends and the process returns to 410, in which the methodology continues to execute 410–460, as described above such as for a duration commensurate with the associated fabrication process. As a result, the present invention facilitates improving semiconductor integrity and reliability, which, in turn, affords increases in quality in accordance with the present invention.

What has been described above includes exemplary implementations of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for measuring characteristics of a substrate, comprising:
   a positioning system having a support operative to receive a substrate, the positioning system being operative to rotate the substrate supported thereby about an axis extending through the support and the substrate;
   a measurement system having a source operative to emit an incident beam onto the substrate; and
   a control system operable to control the source to selectively emit the incident beam based on an angular orientation of the substrate such that the incident beam selectively interrogates a region of the substrate near the axis.

2. The system of claim 1, the source being a light source operative to emit an incident light beam.

3. The system of claim 2, the measurement system further comprising a spectrometer operative to detect at least one of reflected and diffracted light in response to interaction of the incident beam with the substrate, the spectrometer providing a detector signal indicative of optical properties of the at least one of reflected and diffracted light.

4. The system of claim 3, at least one of the measurement system and the control system determining substrate characteristics based on the detector signal.

5. The system of claim 4, further comprising a process system operatively coupled with the control system operative to at least one of apply material onto and remove materials from the substrate during an associated fabrication process, which is monitored by the measurement system.

6. The system of claim 5, the control system being operable to adjust operating characteristics associated with at least one of the positioning system, the process system, and the light source based on the detector.

7. A system for measuring characteristics of a moving substrate, comprising:
   a positioning system having a support for receiving a substrate, the positioning system rotating the substrate supported thereby about an axis; and
   a measurement system having a light source which, when activated, emits an incident light beam onto a central region of the substrate near the axis, the activation of the light source being controlled in synchronization with rotation of the support so as to selectively interrogate the substrate when at a desired orientation relative to the light source.

8. The system of claim 7, the measurement system further comprising a light detector operative to detect a light beam produced in response to the incident beam interacting with the substrate.

9. The system of claim 8, the light detector further comprising a spectrometer, the spectrometer providing a signal indicative of substrate characteristics for a substrate location illuminated by the incident beam.

10. The system of claim 9, further comprising a control system coupled to the positioning system and the measurement system, the control system controlling the light source to emit the incident beam in synchronization with rotation of the substrate, such that the incident beam selectively interrogates the central region of the substrate.

11. The system of claim 10, the substrate having at least one of features and ratings near the central region of the substrate, the control system controlling activation of the light source to emit the incident beam when the at least one of features and ratings are at a desired angular orientation relative to the light source.

12. The system of claim 11, further comprising a process system operatively coupled with the control system and operative to at least one of apply material onto and remove material from the substrate during a fabrication process in which the measurement system is implemented to monitor substrate characteristics.

13. The system of claim 12, the control system being operable to adjust operating characteristics associated with at least one of the positioning system, the process system, and the light source based on the signal indicative of substrate characteristics.

14. The system of claim 12, the means for controlling further comprising means for adjusting operating characteristics associated with at least one of the positioning system, the process system, and the light source based on the substrate characteristics measured during the fabrication process.

15. A system for measuring characteristics of a substrate, comprising:

means for rotating a substrate within a processing environment about an axis;

means for emitting an incident light beam onto the substrate near the axis;

means for detecting at least one of reflected and diffracted light in response to interaction of the incident light beam and the substrate; and means for controlling the means for emitting to intermittently emit the incident light beam onto the substrate near the axis based on the angular orientation of the substrate relative to the means for emitting.

16. The system of claim 15, further comprising means for at least one of applying material onto and removing material from the substrate during a fabrication process, the means for emitting and means for detecting being implemented to measure substrate characteristics during the fabrication process.

17. A method for measuring characteristics of a substrate, comprising:

rotating a substrate about a rotational axis extending through the substrate while supported within a processing environment;

emitting an incident light beam onto the substrate near the rotational axis; and controlling the emitting to emit the incident beam based on the angular orientation of the substrate, whereby the incident beam can selectively interrogate the substrate near the rotational axis when at a desired angular orientation relative to the incident light beam.

18. The method of claim 17, the emitting the incident light beam further comprising intermittently emitting the incident beam when the substrate is at a desired angular orientation relative to the incident light beam.

19. The method of claim 18, further comprising detecting at least one of reflected and diffracted light in response to the incident light beam interacting with the substrate.

20. The method of claim 19, further comprising using a scatterometry technique to discern optical characteristics of the detected light and determining substrate characteristics based on the discerned optical characteristics.

21. The method of claim 20, the substrate including at least one of features and gratings near the rotational axis, the method further comprising controlling the emitting of the incident light beam according to when the at least one of features and ratings are at a desired angular orientation relative to the incident light beam.

22. The method of claim 21, further comprising at least one of applying and removing materials relative to the substrate during a fabrication process, and adjusting operating parameters associated with at least one of the rotating the at least one of applying and removing, and the emitting based on the determined substrate characteristics.

* * * * *